(12) United States Patent
Saroha et al.

(10) Patent No.: US 11,147,513 B2
(45) Date of Patent: Oct. 19, 2021

(54) HANDHELD STEERING DEVICES FOR INTRA VASCULAR DEVICES AND ASSOCIATED SYSTEMS AND METHODS

(71) Applicant: KONINKLIJKE PHILIPS N.V., Eindhoven (NL)

(72) Inventors: Princeton Saroha, Ladera Ranch, CA (US); Jeremy Stigall, Carlsbad, CA (US); Maritess Minas, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 594 days.

(21) Appl. No.: 15/765,615

(22) PCT Filed: Sep. 26, 2016

(86) PCT No.: PCT/IB2016/055732
§ 371 (c)(1),
(2) Date: Apr. 3, 2018

(87) PCT Pub. No.: WO2017/060792
PCT Pub. Date: Apr. 13, 2017

(65) Prior Publication Data
US 2019/0076093 A1   Mar. 14, 2019

Related U.S. Application Data

(60) Provisional application No. 62/239,650, filed on Oct. 9, 2015.

(51) Int. Cl.
*A61B 5/00*  (2006.01)
*A61M 25/01* (2006.01)
(Continued)

(52) U.S. Cl.
CPC ............ *A61B 5/6851* (2013.01); *A61B 5/027* (2013.01); *A61B 5/6852* (2013.01);
(Continued)

(58) Field of Classification Search
CPC ............ A61B 2034/301; A61M 25/01; A61M 25/0113; A61M 25/0105
See application file for complete search history.

(56) References Cited

U.S. PATENT DOCUMENTS

| 5,492,131 A | 2/1996 | Galel |
| 2010/0200636 A1 | 8/2010 | Zemlok |

(Continued)

FOREIGN PATENT DOCUMENTS

| JP | 1991037035 A | 2/1991 |
| JP | 201539395 A | 3/2015 |
| WO | 2009092059 A2 | 7/2009 |

*Primary Examiner* — Puya Agahi

(57) ABSTRACT

Handheld steering devices for use with intravascular devices and associated systems and methods are disclosed. In some instances, the handheld steering device includes a housing sized and shaped for grasping by a hand of a user, the housing including a proximal portion and a distal portion, wherein the distal portion includes an opening sized and shaped to receive an intravascular device; an adaptor positioned within the opening of the housing, the adaptor including a bore sized and shaped to allow a proximal end of the intravascular device to pass therethrough; a steering controller coupled to the housing; and an actuator positioned within the housing and in communication with the steering controller, the actuator interfacing with the proximal end of the intravascular device based on inputs to the steering controller to steer a distal end of the intravascular device. Associated systems and methods are also disclosed.

16 Claims, 12 Drawing Sheets

(51) Int. Cl.
*A61B 5/027* (2006.01)
*A61B 8/08* (2006.01)
*A61B 34/30* (2016.01)
*A61B 34/00* (2016.01)
*A61B 90/00* (2016.01)
*A61B 8/12* (2006.01)
*A61B 8/00* (2006.01)

(52) U.S. Cl.
CPC ....... *A61B 8/0891* (2013.01); *A61M 25/0113* (2013.01); *A61M 25/0133* (2013.01); *A61M 25/0136* (2013.01); *A61M 25/0147* (2013.01); A61B 5/0066 (2013.01); A61B 8/12 (2013.01); A61B 8/445 (2013.01); A61B 34/76 (2016.02); A61B 2034/301 (2016.02); A61B 2034/742 (2016.02); A61B 2090/064 (2016.02); A61M 25/01 (2013.01); A61M 25/0105 (2013.01); A61M 2025/0166 (2013.01)

(56) References Cited

U.S. PATENT DOCUMENTS

| | | |
|---|---|---|
| 2011/0144524 A1* | 6/2011 | Fish ................. A61B 34/10 600/547 |
| 2014/0180124 A1 | 6/2014 | Whiseant et al. |
| 2014/0243734 A1 | 8/2014 | Eubanks et al. |
| 2014/0276594 A1* | 9/2014 | Tanner ............. A61M 25/0147 604/506 |
| 2015/0105615 A1* | 4/2015 | Kato ................. A61B 1/05 600/109 |
| 2015/0272684 A1 | 10/2015 | Tsusaka |
| 2016/0206853 A1* | 7/2016 | Bolduc ............ A61M 25/0133 |
| 2016/0287840 A1* | 10/2016 | Jiang ............... A61M 25/0147 |
| 2017/0258489 A1* | 9/2017 | Galili ............... A61B 17/3403 |

* cited by examiner

US 11,147,513 B2

HANDHELD STEERING DEVICES FOR INTRAVASCULAR DEVICES AND ASSOCIATED SYSTEMS AND METHODS

This application is the U.S. National Phase application under 35 U.S.C. § 371 of International Application No. PCT/IB2016/055732, filed on Sep. 26, 2016, which claims the benefit of Provisional Application Ser. No. 62/239,650, filed Oct. 9, 2015. These applications are hereby incorporated by reference herein.

TECHNICAL FIELD

The present disclosure relates to handheld steering devices for use with intravascular devices used in the diagnosis and treatment of various maladies. In particular, some embodiments disclosed herein are particularly suited for use in intravascular and intracardiac diagnostic procedures and/or treatments.

BACKGROUND

Innovations in diagnosing and verifying the level of success of treatment of disease have migrated from external imaging processes to internal diagnostic processes. In particular, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include angiography, intracardiac echocardiography (ICE), intravascular ultrasound (IVUS), forward looking IVUS (FL-IVUS), pressure sensing (including associated fractional flow reserve (FFR) and instant wave-free ration (iFR) calculations), flow sensing (velocity and/or volumetric measurements, including associated coronary flow reserve (CPR) calculations), optical coherence tomography (OCT), trans-esophageal echocardiography, and various image-guided therapies. Each of these techniques may be better suited for different diagnostic and/or therapeutic situations. To increase the chance of successful treatment, health care facilities may have a multitude of imaging, treatment, diagnostic, and/or sensing modalities on hand in a catheter lab during a procedure. In order to properly use any of the imaging, treatment, diagnostic, and/or sensing modalities, the associated device must be accurately guided to the region of interest within the patient in a controlled manner without causing damage to the anatomy of the patient.

Accordingly, there remains a need for improved intravascular devices, systems, and methods to facilitate the guidance of one or more imaging, treatment, diagnostic, and/or sensing components to a region of interest within a patient.

SUMMARY

Embodiments of the present disclosure are directed to handheld steering devices for use with intravascular devices, including associated systems and methods.

An intravascular steering device is provided that includes a housing sized and shaped for grasping by a hand of a user, the housing including a proximal portion and a distal portion, wherein the distal portion includes an opening sized and shaped to receive an intravascular device; an adaptor positioned within the opening of the housing, the adaptor including a bore sized and shaped to allow a proximal end of the intravascular device to pass therethrough; a steering controller coupled to the housing; and an actuator positioned within the housing and in communication with the steering controller, the actuator interfacing with the proximal end of the intravascular device based on inputs to the steering controller to steer a distal end of the intravascular device.

The steering controller can include a joystick. The actuator can include a first mechanism for controlling movement in a first dimension; and a second mechanism for controlling movement in a second dimension perpendicular to the first dimension. The first and second mechanisms can each include a motor, a pull-wire wheel, and a pull-wire. The actuator can further include a third mechanism for controlling movement in a third dimension, the third dimension being perpendicular to the first and second dimensions. The actuator can further include a mechanism for controlling rotation of the intravascular device about a longitudinal axis of the intravascular device. The intravascular steering device can further include a microcontroller positioned within the housing and in communication with the steering controller and the actuator, wherein the microcontroller translates inputs from the steering controller into actuation signals for the actuator. The intravascular steering device can further include a haptic feedback device positioned within the housing and configured to provide an alert to a user when a force on the intravascular device exceeds a threshold. The force on the intravascular device can be measured by at least one of a sensor within the housing or a sensor within the intravascular device. The intravascular steering device can further include a rechargeable power supply positioned within the housing; and a wireless transceiver positioned within the housing.

An intravascular steering system is also provided that includes an intravascular device having a proximal section and a distal section, wherein at least one sensing component is coupled to the distal section; and an intravascular steering device having: a housing sized and shaped for grasping by a hand of a user, the housing including a proximal portion and a distal portion, wherein the distal portion includes an opening sized and shaped to receive the proximal section of the intravascular device; an adaptor positioned within the opening of the housing, the adaptor including a bore sized and shaped to allow the proximal section of the intravascular device to pass therethrough; a steering controller coupled to the housing; and an actuator positioned within the housing and in communication with the steering controller, the actuator interfacing with the proximal section of the intravascular device based on inputs to the steering controller to steer the distal section of the intravascular device.

A method of steering an intravascular device is also provided that includes providing an intravascular steering device having: a housing sized and shaped for grasping by a hand of a user, the housing including a proximal portion and a distal portion, wherein the distal portion includes an opening sized and shaped to receive a proximal section of an intravascular device; an adaptor positioned within the opening of the housing, the adaptor including a bore sized and shaped to allow the proximal section of the intravascular device to pass therethrough; a steering controller coupled to the housing; and an actuator positioned within the housing and in communication with the steering controller; coupling an intravascular device to the intravascular steering device by introducing a proximal section of the intravascular device through the opening in the housing and through the bore in the adaptor; and utilizing the intravascular steering device to guide the intravascular device to a target location within a patient, wherein inputs to the steering controller cause the actuator to interface with the proximal section of the intravascular device to steer a distal section of the intravascular device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

Figure 1:
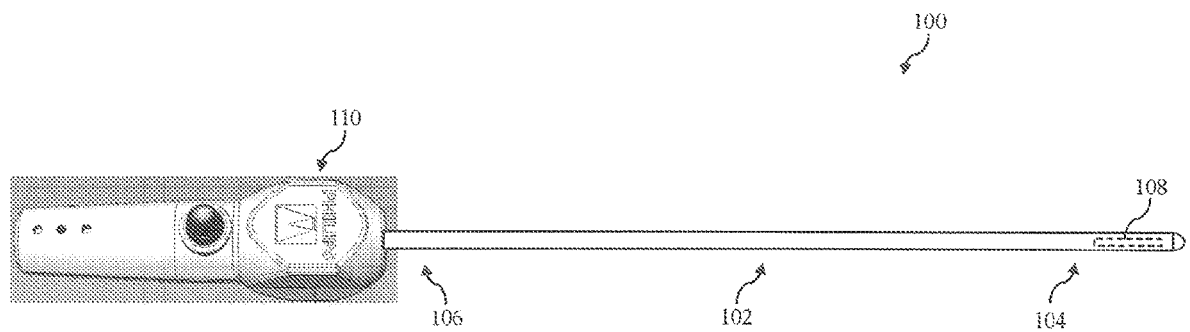
FIG. 1 is a perspective view of an intravascular system including a handheld steering device and an intravascular device according to the present disclosure.

For clarity of discussion, elements having the same designation in the drawings may have the same or similar functions. The drawings may be better understood by referring to the following Detailed Description.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a flow sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm), approximately 0.018" (0.4572 mm), and approximately 0.035" (0.889 mm). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is a system 100 that includes an intravascular device 102 and a steering device 110. As discussed in greater detail below, a proximal portion of the intravascular device 102 is engaged with the steering device 110 such that the steering device 110 can be utilized to steer a distal portion of the intravascular device 102. In this regard, the steering device 110 provides a user with an ergonomic and intuitive controller for accurately and precisely controlling the movement of a disposable intravascular device (e.g., multi-planar steering, withdrawal, advancement, rotational, and/or combinations thereof) within a patient. As a result, the steering device 110 provides many advantages and improvements over existing approaches, including without limitation: single hand operation/control in all actuation directions, simple and intuitive functional interface, improved actuation precision including speed and angle differentiation, fast yet controlled actuation response, minimum user force input required for actuation (actuation strength limited by motor specifications instead of user comfort), ability to use with many different types of intravascular devices with varying profiles/characteristics, safety lock and return to neutral position functionalities, minimum bend radius, reduced body sway when actuating the distal tip, better torque response, disposable, lower cost, easier manufacturability and assembly, modular componentry to facilitate simple manufacture and/or assembly of numerous specialized devices.

The steering device 110 can also be implemented with various advanced control features to further improve the functionality of the device and associated user experience. For example, the steering device 110 may include one or more of the following features: memory for storing and recalling position(s) and/or actuation angle(s) in a controlled manner, including allowing the setting of different positions as the neutral intravascular device position, providing the user accurate feedback on the intravascular device's position/actuation angle relative to home (neutral) position, allowing control of the steering device by a remote user (e.g., at the system console, in a separate room, and/or across the world), multi-level actuation controls (e.g., coarse, fine, etc.), logging actuation usage for complaint handling and/or case documentation, providing automated 3D anatomical mapping of the vessels, heart, or other structures when used in conjunction with intravascular devices having imaging elements, and producing more consistent device control through in line calibrations for both first time device use and repeated uses after reprocessing, which can reduce unit to unit variation and compensate for the effects of wear and tear on the steering device and/or intravascular device.

The intravascular device 102 includes a flexible elongate member having a distal portion 104 adjacent a distal end and a proximal portion 106 adjacent a proximal end. A component 108 is positioned within the distal portion 104 of the flexible elongate member proximal of the distal end. Generally, the component 108 is representative of one or more electronic, optical, or electro-optical components. In that regard, the component 108 can include an imaging element, an optical fiber, an ultrasound transducer, a reflector, a mirror, a prism, an ablation element, an RF electrode, a pressure sensor, a flow sensor, a temperature sensor, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned within a housing of the intravascular device 102. In that regard, the housing is a separate component secured to the flexible elongate member in some instances. In other instances, the housing is integrally formed as a part of the flexible elongate member.

In some instances, the intravascular device 102 also includes a connector adjacent the proximal portion 106 of the device. In that regard, the connector can be at the proximal end of the flexible elongate member or spaced from the proximal end of the flexible elongate member. Generally, the spacing from the proximal end can be between 0% and 50% of the total length of the flexible elongate member. While the total length of the flexible elongate member can be any length, in some embodiments the total length is between about 1300 mm and about 4000 mm, with some specific embodiments having a length of 1400 mm, 1900 mm, and 3000 mm. Accordingly, in some instances the connector is positioned at the proximal end. In other instances, the connector is spaced from the proximal end. For example, in some instances the connector is spaced from the proximal end between about 0 mm and about 1400 mm. In some specific embodiments, the connector is spaced from the proximal end by a distance of 0 mm, 300 mm, and 1400 mm. In some implementations, the connector is positioned at or adjacent to the proximal end of the intravascular device 102 such that the connector engages a mating connector within the steering device 110 when the intravascular device 102 is coupled with the steering device 110. In other implementations, the connector is spaced from the proximal end of the intravascular device 102 such that the connector is positioned outside of the steering device 110 when the intravascular device 102 is coupled with the steering device 110, which can allow selective coupling of the connector to a mating connector separate from the steering device 110.

The connector is configured to facilitate communication between the intravascular device 102 and another device. More specifically, in some embodiments the connector is configured to facilitate communication of data obtained by the component 108 to another device, such as a computing device or processor. Accordingly, in some embodiments the connector is an electrical connector. In such instances, the connector provides an electrical connection to one or more electrical conductors that extend along the length of the intravascular device 102 and are electrically coupled to the component 108. In some embodiments the electrical conductors are embedded within a core of the flexible elongate member. In other embodiments, the connector is an optical connector. In such instances, the connector provides an optical connection to one or more optical communication pathways (e.g., fiber optic cable) that extend along the length of the intravascular device 102 and are optically coupled to the component 108. Similarly, in some embodiments the optical fibers are embedded within a core of the flexible elongate member. Further, in some embodiments the connector provides both electrical and optical connections to both electrical conductor(s) and optical communication pathway(s) coupled to the component 108. In that regard, it should be noted that component 108 can be comprised of a plurality of elements. The connector can be configured to provide a physical connection to another device, either directly or indirectly. The connector can also be configured to facilitate wireless communication between the intravascular device 102 and another device. Generally, any current or future developed wireless protocol(s) may be utilized. In yet other instances, the connector facilitates both physical and wireless connection to another device.

As noted above, in some instances the connector provides a connection between the component 108 of the intravascular device 102 and an external device. Accordingly, in some embodiments one or more electrical conductors, one or more optical pathways, and/or combinations thereof extend along the length of the intravascular device 102 between the connector and the component 108 to facilitate communication between the connector and the component 108. Generally, any number of electrical conductors, optical pathways, and/or combinations thereof can extend along the length of the intravascular device 102 between the connector and the component 108, embedded in the core or not. In some instances, between one and ten electrical conductors and/or optical pathways extend along the length of the intravascular device 102 between the connector at the proximal portion 106 and the component 108 at the distal portion 104. The number of communication pathways and the number of electrical conductors and optical pathways extending along the length of the intravascular device 102 is determined by the desired functionality of the component 108 and the corresponding elements that define component 108 to provide such functionality.

Figure 2:
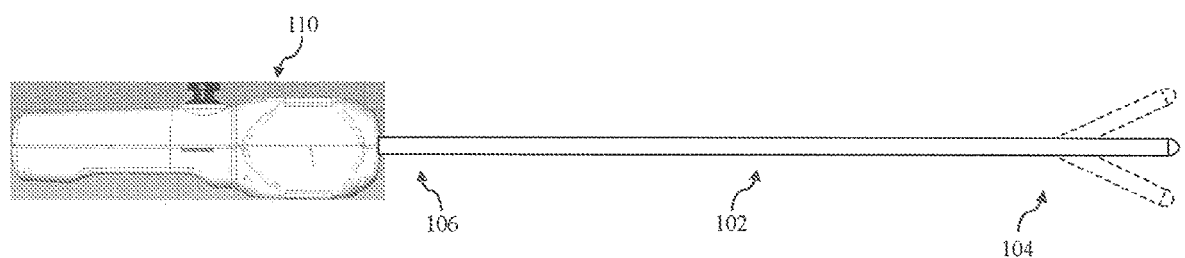
FIG. 2 is a side view of the intravascular system of FIG. 1 showing steering of the intravascular device by the handheld steering device in a first dimension (e.g., up and down).
Figure 3:
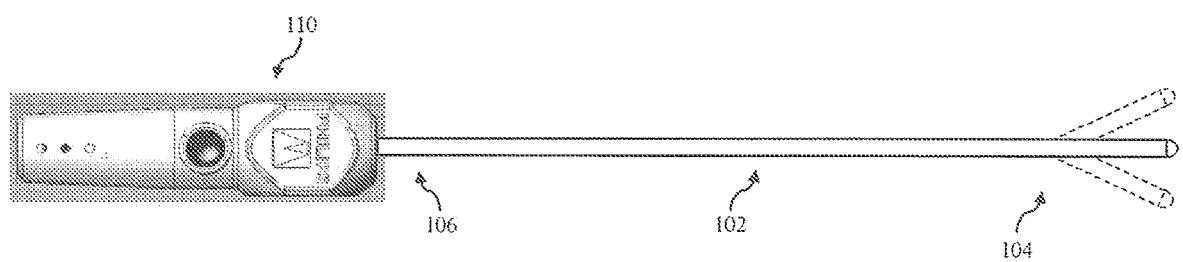
FIG. 3 is a top view of the intravascular system of FIGS. 1 and 2 showing steering of the intravascular device by the handheld steering device in a second dimension (e.g., left and right), the second dimension being perpendicular to the first dimension shown in FIG. 2.

As noted above, the steering device 110 is configured to control movement of the distal portion 104 of the intravascular device 102 by interfacing with the proximal portion 106 of the intravascular device 102. In this regard, the steering device 110 can be configured to control movement of the distal portion 104 of the intravascular device 102 in one or more dimensions. For example, FIGS. 2-5 show various types of movements that can be controlled by the steering device 110. Referring to FIG. 2, the steering device 110 is shown controlling movement of the distal portion 104 of the intravascular device 102 in a first dimension (e.g., up and down relative to the steering device 110). Referring to FIG. 3, the steering device 110 is shown controlling movement of the distal portion 104 of the intravascular device 102 in a second dimension (e.g., left and right relative to the steering device 110) that is perpendicular to the dimension shown in FIG. 2. While FIGS. 2 and 3 show particular, exemplary deviations of the distal portion 104 of the intravascular device 102 in the noted dimensions, it is understood that actuation of the steering device 110 in a particular direction can cause the distal tip of the intravascular device 102 to move between 0 degrees and 180 degrees (or more) in that direction depending on the amount of actuation imparted by the user. Accordingly, in some implementations continued actuation of the steering device 110 in a particular direction can cause the distal portion 104 of the intravascular device 102 to contact and/or loop next to a more proximal portion of the intravascular device 102.

Figure 4:
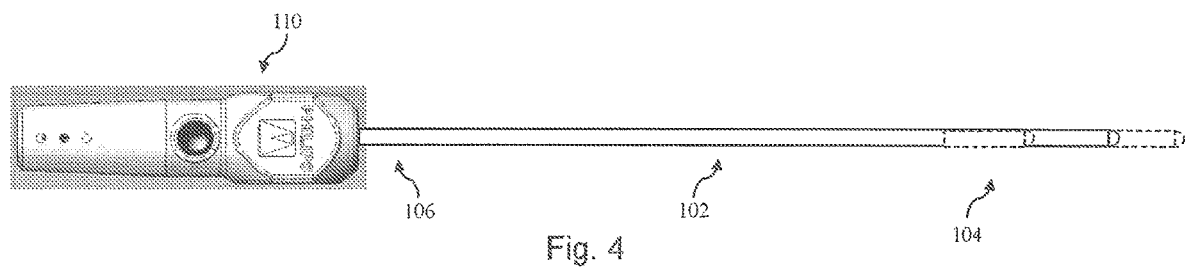
FIG. 4 is a top view of the intravascular system of FIGS. 1-3 showing translation of the intravascular device by the handheld steering device in a third dimension (e.g., forward and backward), the third dimension being perpendicular to the first and second dimensions shown in FIGS. 2 and 3.

Referring to FIG. 4, the steering device 110 is shown controlling movement of the distal portion 104 of the intravascular device 102 in a third dimension (e.g., forward and backward relative to the steering device 110) that is perpendicular to the dimensions shown in FIGS. 2 and 3. In particular, FIG. 4 shows the steering device 110 controlling translation of the intravascular device 102 along a longitudinal axis of the intravascular device. In some implementations, the steering device 110 can be utilized to precisely control the advancement or retraction of the intravascular device 102 through a patient, including the distance, speed, and/or combination thereof. In this regard, the steering device 110 can be utilized to perform pullback procedures to obtain data over a length of a region of interest within the patient.

Figure 5:
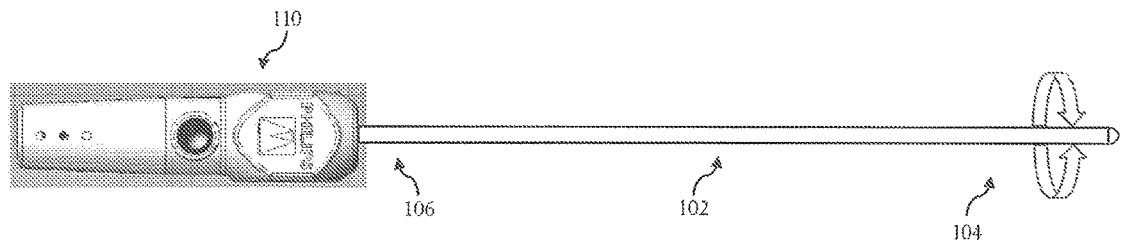
FIG. 5 is a top view of the intravascular system of FIGS. 1-4 showing rotation (e.g., clockwise and/or counter-clockwise) of the intravascular device by the handheld steering device.

Referring to FIG. 5, the steering device 110 is shown controlling rotation of the distal portion 104 of the intravascular device 102 about a longitudinal axis of the intravascular device. In some implementations, the steering device 110 can be utilized to precisely control the rotational position of the distal portion 104 of the intravascular device 102 to facilitate aiming or positioning of the distal portion 104 of the intravascular device in a desired manner. For example, this can be useful for ablation procedures, repositioning a sensing element (e.g., when an ambient opening for a pressure sensor is positioned against a vessel wall, rotation of the distal portion of the intravascular device can move the opening towards the center of the vessel to improve the accuracy of pressure measurements), and/or other instances where a rotational orientation of the intravascular device 102 can affect the diagnosis and/or treatment.

The steering device 110 can be configured to control movement of the distal portion 104 of the intravascular device 102 in one or more of the manners shown in FIGS. 2-5, including all of them in some implementations. The particular movement(s) that the steering device 110 is configured to control may be selected based on the type(s) of intravascular devices the steering device is to be used with, user preference, and/or other factors. Further, it is understood that various types of electro-mechanical, mechanical, pneumatic, optical-mechanical components, and/or combinations thereof can be utilized within the steering device 110 to impart forces on the proximal portion 106 of the intravascular device 102 to control the movement of the distal portion 104 of the intravascular device 102 in the desired direction(s). Some exemplary approaches and components are described below, but this does not limit the types of approaches or components that can be utilized within the steering device 110 to impart such movements.

Figure 6A:
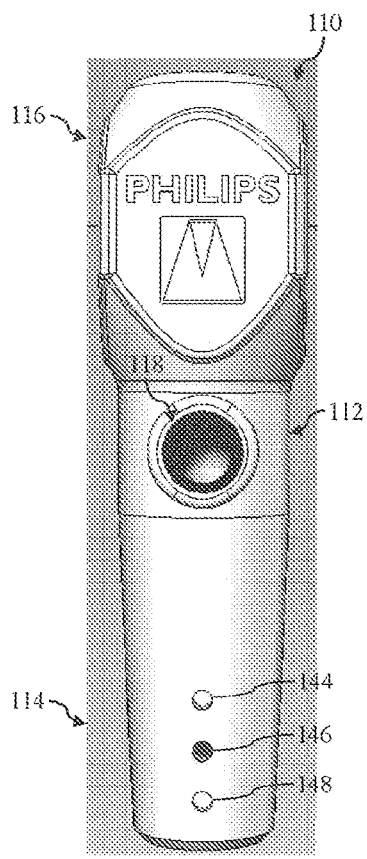
FIG. 6A is a top view of the handheld steering device of FIGS. 1-5.
Figure 6B:
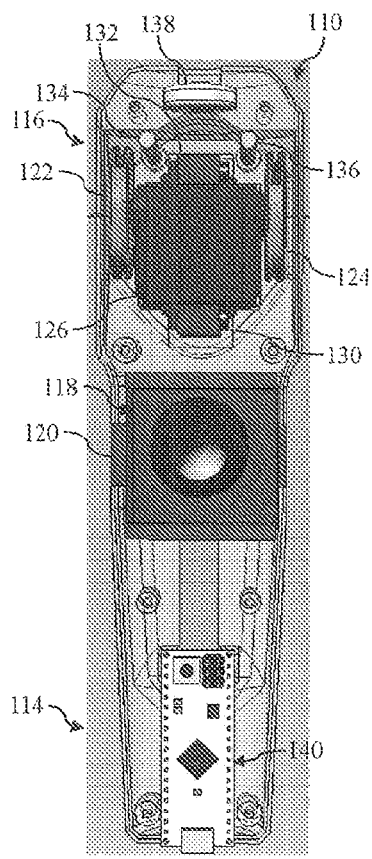
FIG. 6B is a top view of the handheld steering device similar to that of FIG. 6A, but with a top portion of a housing of the handheld steering device removed to reveal inner components of the handheld steering device.

Referring now to FIGS. 6A-14B, additional details of the steering device 110 will be described. Referring initially to FIG. 6A, the steering device 110 includes a housing 112 having a proximal portion 114 and a distal portion 116. The housing 112 is sized and shaped for grasping by a single hand of a user. It is understood that the housing 112 may have many different geometries suitable for handheld use other than those shown in the present disclosure. The steering device 110 also includes a steering controller 118 coupled to the housing 112. The steering controller 118 can be any suitable type of controller including without limitation a joystick (as shown), dial, track pad, scroll wheel, touchscreen, and/or combinations thereof. In short, the steering controller 118 should be able to receive user inputs indicative of a desired movement of the distal portion 104 of the intravascular device 102. The steering controller 118 may include multiple controls in some instances. For example, the steering controller 118 may include separate control for each dimension or a separate control for a combination of dimensions (e.g., a control for x-y movements).

A single thumb joystick can be particular suitable for controlling steering of the distal portion of the intravascular device 102 in all directions. In this regard, the joystick circuit can include a biaxial potentiometer design with a digital button pin press function. The joystick circuit can be connected to a microcontroller. Through software and/or firmware coding, a variety of functions can be controlled through a single joystick. For example, the use of a single click, double clicks, press for duration, etc. can be utilized to toggle the joystick between different functions/controls. However, additional buttons controlling specific handle functionalities (e.g. on/off switch, lock button, etc.) can be included in addition to the joystick for user convenience and ease of use.

As shown in FIGS. 6B, 6C, 13B, and 14B, the steering controller 118 is coupled to a mount 120. The mount 120 is coupled to the housing 112. The mount 120 is sized and shaped such that when the steering controller 118 is positioned on the mount 120, the steering controller 118 is positioned at a desired orientation with respect to the housing 112. In this regard, the structure of the mount 120 can be selected based on structural aspects of the steering controller 118 and/or the housing to facilitate the desired alignment of the steering controller 118 with respect to the housing 112. In the illustrated embodiment, the mount 120 is coupled to the housing 112. In particular, the mount 120 is coupled to a lower housing portion 112*b* with the help of keyed interfaces (circular keyed interface below the mount 120 for centering, and horizontal keyed interfaces with the side walls for vertical alignment and to prevent rotation.

As shown in FIGS. 6B, 6C, 7, 13B, and 14B, the steering device 110 includes pull-wire wheels 122 and 124, pull-wires 123 and 125 (FIG. 6C), motors 126 and 128, mounting structures 130 and 132, and guide pins 134 and 136. In this regard, motor 126 is coupled to pull-wire wheel 122 to control movement of the intravascular device 102 in a first dimension (e.g., up and down), while motor 128 is coupled to pull-wire wheel 124 to control movement of the intravascular device 102 in a second dimension (e.g., left and right). The motors 126 and 128 are mounted onto the mounting structures 130 and 132, which are coupled to the housing 112. The mount structures 130 and 132 are sized and shaped such that when the motors 126 and 128 are positioned on the mounting structures 130 and 132, the pull-wire wheels 122 and 124 mounted to the motors 126 and 128, respectively, will be positioned at a desired location with respect to the guide pins 134 and 136. In this regard, the guide pins 134 and 136 can be utilized to tension the pull-wires 123 and 125 that interface with the proximal portion 106 of the intravascular device 102.

More specifically, the pull-wires 123 and 125 exit the pull-wire wheels 122 and 124 and are routed around the guide pins 134 and 136 such that when the intravascular device 102 is received within the steering device 110 the pull-wires 123 and 125 will interface with the proximal portion of the intravascular device 102. The guide pins 134 and 136 can be slotted into the housing 112 to provide a safe and controlled pathway for the pull-wires 123 and 125 to navigate to the pull-wire wheels 122 and 124. The guide pins 134 and 136 can be of various geometries to control the angle and pathway of the pull-wires 123 and 125. In addition to or as an alternative to the guide pins 134 and 136, the steering device 110 can include grooves, slots, projections, tapers, and/or other structures integrally formed as part of the housing 112 to safely guide the pull-wires 123 and 125.

Selective actuation of the motors 126 and 128 in response to user inputs to the steering controller 118 imparts tension on the pull-wires 123 and 125 in a particular direction (based on the direction of rotation of the motor and associated pull-wire wheel corresponding to the user inputs), causing the proximal portion 106 of the intravascular device 102 to be moved in a corresponding manner and imparting movement to the distal portion 104 of the intravascular device 102. In the illustrated embodiment, two pull-wire wheels 122 and 124 attached to two different motors 126 and 128 are controlled by a single steering controller 118 (a joystick with biaxial potentiometer in the illustrated embodiment) to facilitate steering of the intravascular device in all directions in a plane extending perpendicular to a longitudinal axis of the intravascular device.

Figure 12A:
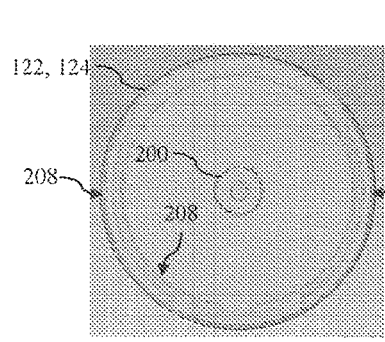
FIG. 12A is a front view of a pull-wire wheel of the handheld steering device.
Figure 12B:
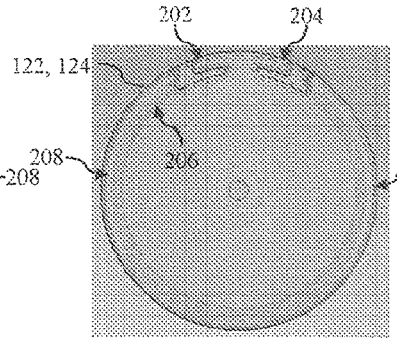
FIG. 12B is a back view of the pull-wire wheel of FIG. 12A.
Figure 12C:
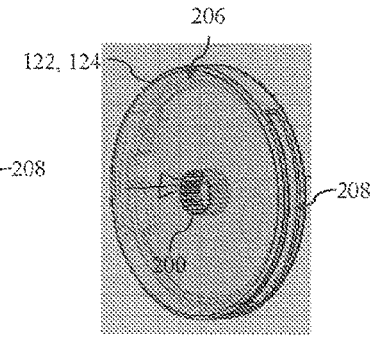
FIG. 12C is a perspective view of the pull-wire wheel of FIGS. 12A and 12B.
Figure 13A:
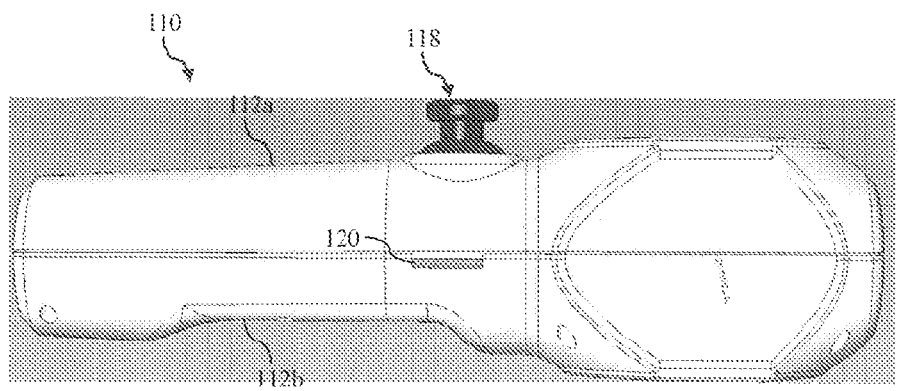
FIG. 13A is a side view of the handheld steering device of FIGS. 1-7.
Figure 13B:
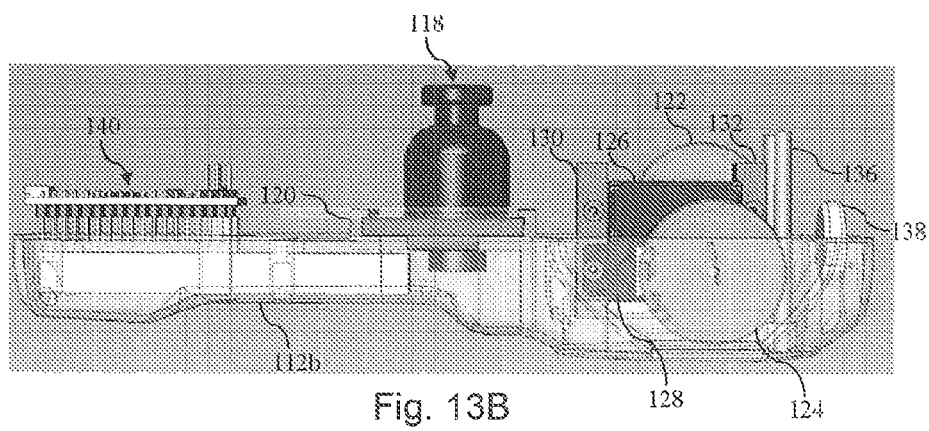
FIG. 13B is a side view of the handheld steering device similar to that of FIG. 13A, but with a top portion of a housing of the handheld steering device removed to reveal inner components of the handheld steering device.
Figure 14A:
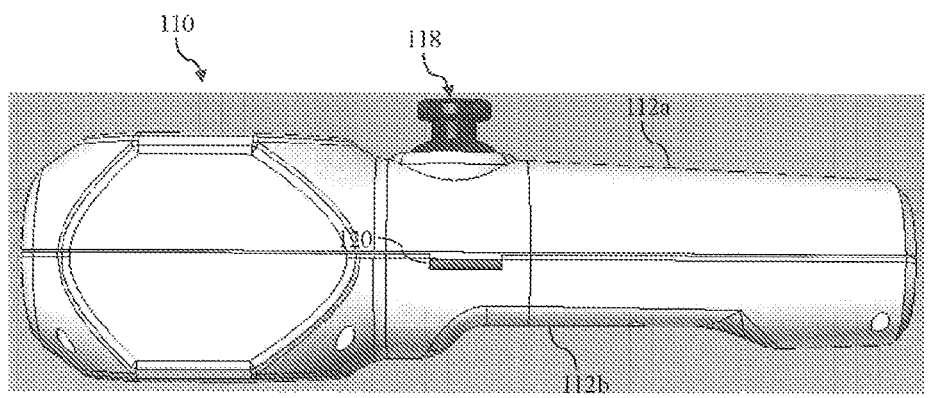
FIG. 14A is a side view of the handheld steering device similar to that of FIG. 13A, but from the opposing side.
Figure 14B:
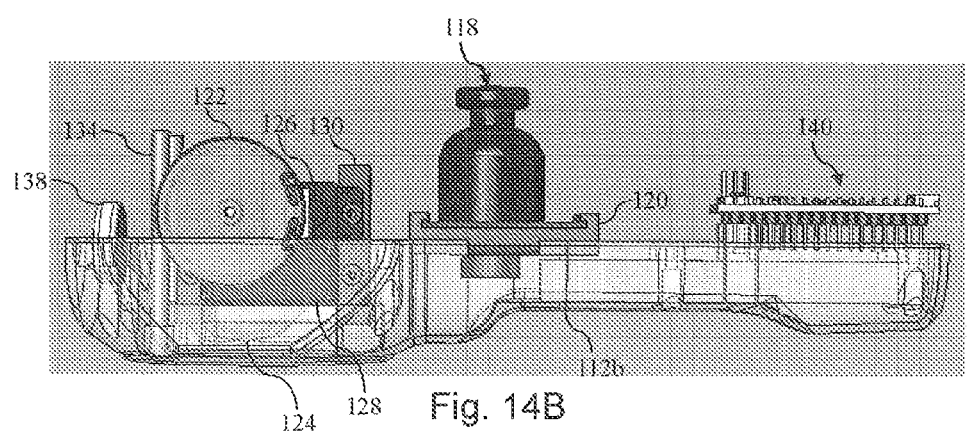
FIG. 14B is a side view of the handheld steering device similar to that of FIG. 14A, but with a top portion of a housing of the handheld steering device removed to reveal inner components of the handheld steering device.

FIGS. 12A-12C illustrate additional aspects of the pull-wire wheels 122 and 124. The pull-wire wheels 122 and 124 are sized and shaped to facilitate steering precision in a repeatable manner. All surfaces contacting the pull-wires 123 and 125 are radii used or curved to prevent sharp edges from biting into the pull-wire material. The pull-wire wheels 122 and 124 are configured to interface with the motors 126 and 128. In this regard, the pull-wire wheels 122 and 124 include a notched or keyed opening 200 to engage with a corresponding notched or keyed wheel of the motors 126 and 128.

The pull-wire wheels 122 and 124 also include anchor structures 202 and 204 that are in communication with a partially enclosed pull-wire track 206. In this regard, the internal pull-wire track 206 prevents the pull-wires 123 and 125 from misaligning as pull-wires cycle through periods of relaxation and high tension as the intravascular device 102 is steered in various directions. The internal pull-wire track 206 also helps ensure that the pull-wire location at high tension relative to the wheel itself is more consistent through several actuations, allowing for more flexible placement of the wheels relative to the proximal end of the intravascular device 102. The pull-wires 123 and 125 are thread through the internal pull-wire tracks of the pull-wire wheels 122 and 124, secured around the anchor structures 202 and 204, and terminated.

The pull-wire wheels 122 and 124 include openings 208 through which the pull-wires 123 and 125 extend to the guide pins 134 and 136 for interfacing with the proximal end of the intravascular device 102. In this regard, the angle of the openings 208 can be optimized to maximize the actuation of the steering device 110 (e.g., to achieve greatest net force created when steering in a particular direction). The optimal angle will be dependent on such factors as the pathway of the pull-wires 123 and 125 to the pull-wire wheels 122 and 124, the relative location of the pull-wire wheels 122 and 124 to the proximal end of the intravascular device 102, and the range of the motors being used, etc.

The motors 126 and 128 can include stepper motors, servo motors, and/or other suitable motor. The motors can be mounted either on fixed brackets attached to or integrally formed with the housing or onto removable brackets, such as the mounting structures 130 and 132, that are removably coupled to the housing 112 (e.g., through a keyed or interlocking interface). The use of removable brackets can allow for more flexibility in motor selection and actuation design for the steering device 110. For example, several different mounting structures can be provided for used with a variety of different motors and/or other actuating mechanism for use within the same housing 112.

Figure 15A:
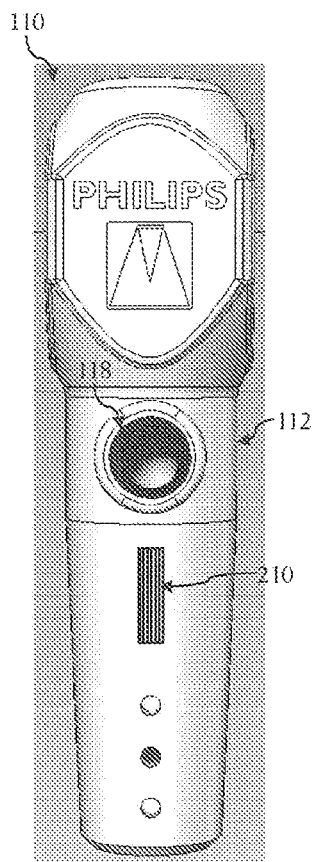
FIG. 15A is a top view of a handheld steering device having a scroll wheel for controlling translation of an intravascular device.

Further, in some instances some or all components of the actuator system (e.g., motors 126 and 128, the mounting structures 130 and 132, and/or the guide pins 134 and 136) can be attached to a rail or track extending along a length of the housing 112. In this regard, the actuator system can be moved along the length of the housing 112 to facilitate translational movement of the intravascular device, alone or in combination with other directional movements. Movement of the actuator system can be accomplished using a gear and chain mechanism coupled to a motor or other suitable translation mechanism. If translational actuation is provided by the steering device 110, then the steering device 110 may receive inputs regarding the desired translation from the steering controller 118. In some instances, a mode of operation of the steering controller 118 is selected/changed to distinguish between z-dimension steering inputs (i.e., forward and backward) and x-y steering inputs (i.e., up, down, left, and right). Alternatively, the steering device may include a separate controller to receive inputs with respect to the desired translation actuation. For example, FIG. 15A illustrates a steering device 110 with a separate controller 210 for controlling translational movement of the intravascular device 102. In the illustrated embodiment, the controller 210 is a scroll wheel, but other controller such as a joystick, dial, track pad, touchscreen, etc. may be utilized.

Figure 15B:
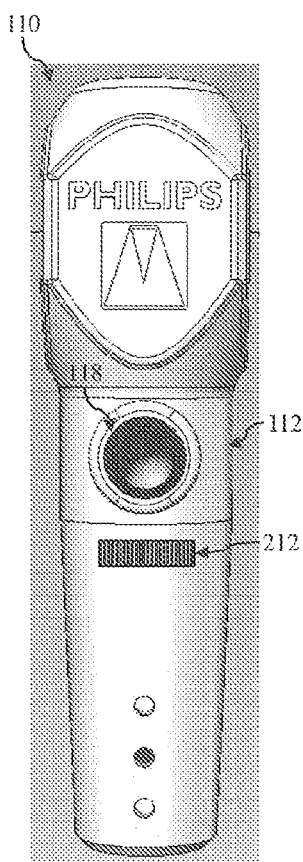
FIG. 15B is a top view of a handheld steering device having a scroll wheel for controlling rotation of an intravascular device.
Figure 15C:
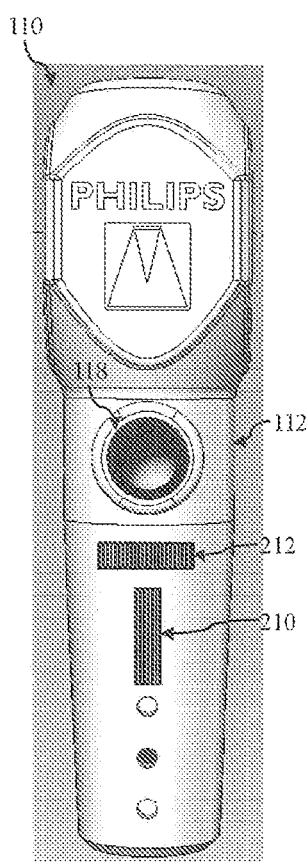
FIG. 15C is a top view of a handheld steering device having a scroll wheels for controlling rotation and/or translation of an intravascular device.

If rotational actuation is provided by the steering device 110, then the steering device 110 may receive inputs regarding the desired rotation from the steering controller 118. In some instances, a mode of operation of the steering controller 118 is selected/changed to distinguish between rotational steering inputs (i.e., clockwise and/or counter-clockwise about the longitudinal axis of the intravascular device) and x-y-z dimension steering inputs (i.e., forward, backward, up, down, left, and/or right). Alternatively, the steering device may include a separate controller to receive inputs with respect to the desired rotational actuation. For example, FIG. 15B illustrates a steering device 110 with a separate controller 212 for controlling rotational movement of the intravascular device 102. In the illustrated embodiment, the controller 212 is a scroll wheel, but other controller such as a joystick, dial, track pad, touchscreen, etc. may be utilized. Further, FIG. 15C illustrates a steering device 110 with separate controllers 210 and 212 for controlling translation and rotational movement of the intravascular device 102, respectively.

The range of rotation imparted by the scroll wheel can restricted to prevent over torqueing the intravascular device. In this regard, the range of rotation can be restricted mechanically and/or electronically. For example, the scroll wheel may provide a mechanical interface to the intravascular device such that rotation of intravascular device is directly proportional to the range of motion of the scroll wheel. In such instances, the scroll wheel may include stops that limit a range of motion of the scroll wheel to a desired range (e.g., 90 degrees, 180 degrees, 270 degrees, 360 degrees, 450 degrees, 540 degrees, or other suitable range) and, thereby, limit the range of rotation of the intravascular device.

Similarly, the range of rotation can be electronically controlled where an electro-mechanical interface is utilized to control rotation. For example, where inputs to the scroll wheel are converted into corresponding actuation of a motor and keyed/geared interface to cause rotation of the intravascular device, the range of the motor can be electronically limited to stay within the desired range of rotation. In some instances, there is no limitation to the range of rotation. For example, in some implementations it may be desirable to repeatedly rotate the intravascular device or a portion thereof (such as an internal drive shaft). In such instances, DC motors can be used where rapid rotational actuation is desired (e.g., rotating a drive shaft coupled to an imaging element, such as an IVUS transducer or OCT element, at the distal portion of the intravascular device).

As shown in FIGS. 6B, 6C, 7, 10A, 10B, 11A, 11B, 13B, and 14B, to facilitate secure, but removable engagement of the proximal portion 106 of the intravascular device 102 with the steering device 110, the steering device 110 includes an adaptor 138. The adaptor is positioned within an opening in the distal portion of the housing 112 that is sized and shaped to receive an intravascular device. However, the opening in the housing 112 may be large enough to receive intravascular devices of various sizes such that the steering device 110 is suitable for use with a variety of different intravascular devices. Accordingly, the size of the adaptor 138 can be selected based on the particular intravascular device(s) that the steering device 110 will be used with. In this regard, in some instances the steering device 110 is provided with a plurality of adaptors 138 of varying sizes to allow the user to select and install the appropriate adaptor 138 within the steering device.

Figure 6C:
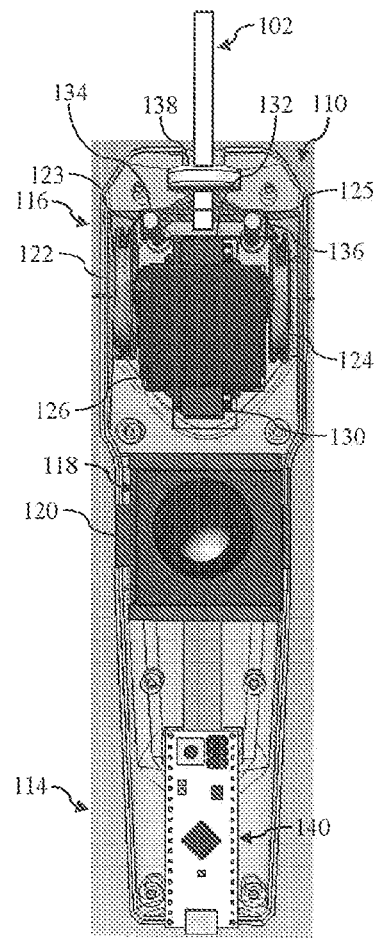
FIG. 6C is a top view of the handheld steering device similar to that of FIG. 6B, but showing an intravascular device engaged with the handheld steering device.
Figure 7:
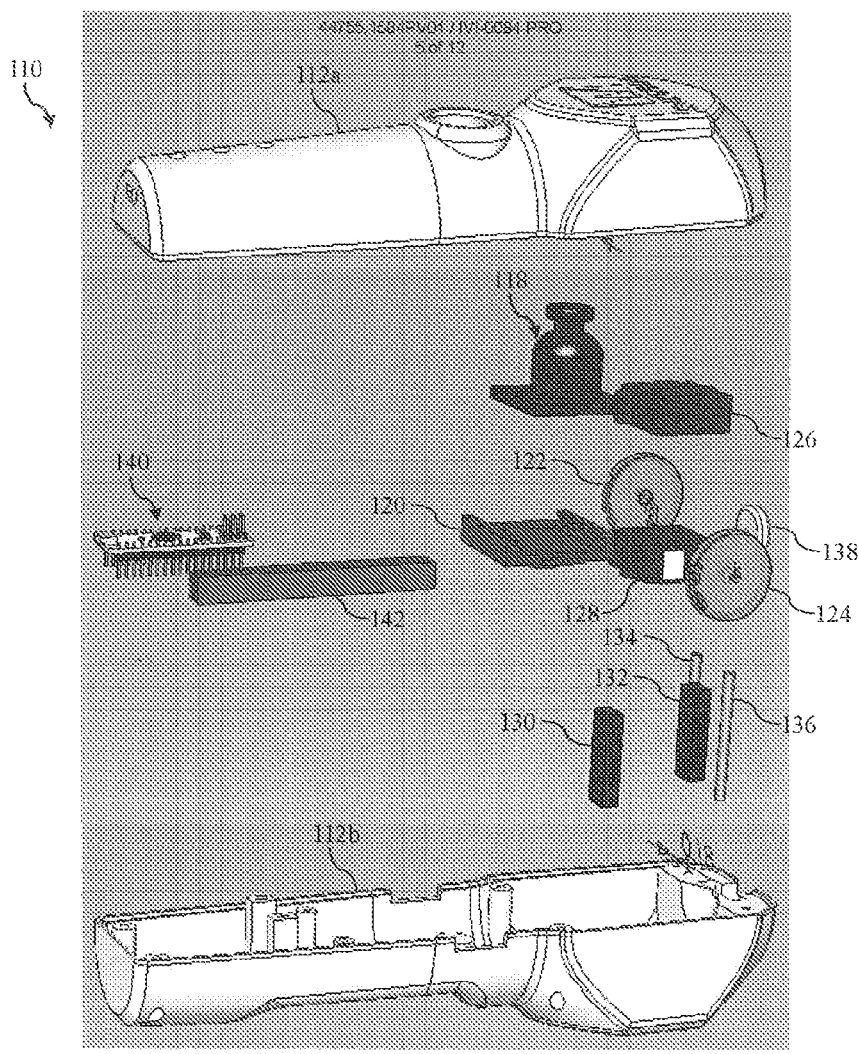
FIG. 7 is an exploded, perspective view of the handheld steering device of FIGS. 1-6C.
Figure 10A:
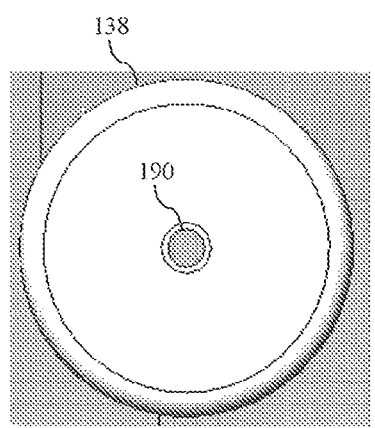
FIG. 10A is a front view of a shaft adapter of the handheld steering device.
Figure 10B:
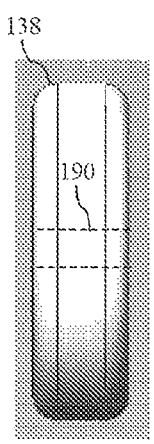
FIG. 10B is a side view of the shaft adapter of FIG. 10A.

FIGS. 10A and 10B illustrate an embodiment of the adaptor 138 having a bore 190 extending therethrough. The bore 190 is sized and shaped to allow the proximal end of an intravascular device to pass therethrough to interface with the steering actuators of the steering device 110 (as shown in FIG. 6C, for example). However, the bore 190 is also sized and shaped to provide an interference fit with the proximal portion of the intravascular device 102 such that the intravascular device 102 remains engaged with the steering device 110. Accordingly, in some implementations the bore 190 is sized to be equal to or smaller than the outer diameter of the proximal portion 106 of the intravascular device 102. In this regard, the adaptor 138 can be formed of a material with sufficient flexibility to allow slight deformation of the adaptor 138 (e.g., expansion of the bore 190) such that the intravascular device 102 can be selectively inserted and removed from the adaptor 138.

Figure 11A:
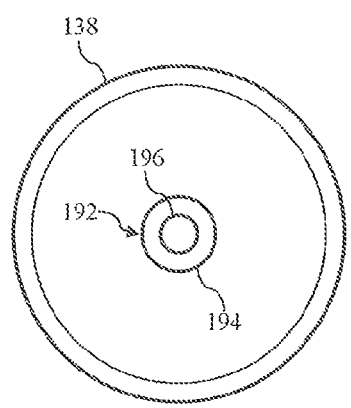
FIG. 11A is a front view of a shaft adapter of the handheld steering device.
Figure 11B:
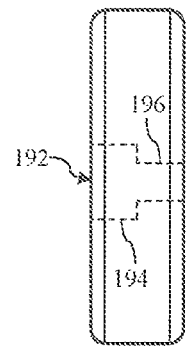
FIG. 11B is a side view of the shaft adapter of FIG. 11A.

FIGS. 11A and 11B illustrate an embodiment of the adaptor 138 having a variable bore 192 extending therethrough. In particular, the bore 192 includes a section 194 and a section 196. The section 194 has a larger diameter than the section 196, as shown. In some implementations, the sections 194 and 196 are configured to receive and/or engage different portions of an intravascular device. For example, the section 194 can be sized and shaped to receive an outer sleeve or jacket of an intravascular device, while the section 196 is sized and shaped to allow an inner shaft of the intravascular device to pass therethrough to interface with the steering actuators of the steering device 110. In some specific implementations, the section 194 loosely engages the outer sleeve or jacket such that the outer sleeve or jacket is rotatable with respect to the adaptor 138, while the section 196 has an interference fit with the inner shaft of the intravascular device. Using such an interface, the outer sleeve or jacket of the intravascular device can be held in place with respect to the steering device 110 via a keyed interface that prevents separation, but still allows for rotational actuation of the outer sleeve or jacket.

In the illustrated embodiment, the adaptor 138 is positioned within the housing 112. However, in some embodiments, the adaptor 138 is part of a separate component attachable to the distal end of the external handle housing. In this situation, the pull-wires 123 and 125 associated with the pull-wire wheels 122 and 124 can include mating mechanisms to interface with corresponding pull-wires of the separate component containing the adaptor 138. In this manner, a universal handle with steering wires can be provided and then separate add-on components with appropriately sized adaptors can be provided for different types and sizes of intravascular devices. The pull-wires and mating components can be placed in alignment with one another along the surfaces of the attachable adapter and the distal surface of the housing for ease of attachment (e.g., single click and rotation to mate all the pull-wires together and lock the adaptor securely in place with respect to the housing 112). The attachable modular shaft adapter concept allows for quick replacement and immediate handle integration of a variety of shaft types and devices during manufacturing, reprocessing, and/or during a diagnostic/treatment procedure.

As shown in FIGS. 6B, 6C, 7, 13B, and 14B, the steering device 110 includes a microcontroller 140. The microcontroller 140 can be utilized to control the logic and store the data and/or program code necessary for actuation and/or advanced features of the steering device 110. In this regard, it is understood that the microcontroller 140 can include a processor, which may be implemented using a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. The processor may also be implemented as a combination of computing devices, e.g., a combination of a DSP and a microprocessor, a plurality of microprocessors, one or more microprocessors in conjunction with a DSP core, or any other such configuration.

It is also understood that the microcontroller 140 can include memory, which may include random access memory (RAM), read-only memory (ROM), flash memory devices in RAM, optical storage media, erasable programmable read-only memory (EPROM), registers, or combinations thereof, including a non-transitory computer-readable medium. Instructions or code may be stored in the memory of the microcontroller 140 that are executable by a processor of the microcontroller. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The microcontroller 140 can power the motors and/or other actuators needed for the full range of steering actuations provided by the steering device 110. The microcontroller 140 can be powered through a wired interface with an external device (e.g., processing system, console, etc.) or via a rechargeable power supply (e.g., one or more batteries, capacitors, etc.) within the housing 112. To this end, a mounting structure 142 onto which the microcontroller 140 is mounted within the housing 112 can be and/or include one or more power supplies. Alternatively, the power supply can be positioned elsewhere within the housing 112 and/or removably coupled to the housing 112.

As shown in FIG. 6A, the steering device 110 can include indicator lights 144, 146, and 148. The indicator lights 144, 146, and 148 can provide various indications to the user as to the state of the steering device 110 and/or the intravascular device 102. The indicator lights 144, 146, and 148 may be provided in addition to other notifications to the user, for example via a graphical user interface of an associated processing system. The indicator lights can provide a wide variety of notifications to the user, include without limitation: on/off, device at HOME position, device at STORED position, device moving to HOME, device moving to STORED position, device position locked, motor(s) at maxed position in a particular direction, etc. In this regard, the indicator lights 144, 146, and 148 can be part of or in communication with the microcontroller 140 such that the microcontroller 140 controls the activation/status of the indicator lights 144, 146, and 148.

In addition to and/or in lieu of the indicator lights 144, 146, and 148, the steering device 110 can include other indicators, including audible and tactile notifications. For example, in some implementations the steering device 110 is configured to provide force feedback to the user based on force sensors at the distal portion of the intravascular device (monitoring the amount of force/compression on the distal portion of the intravascular device) and/or force sensors monitoring the amount of tension of the pull-wires and/or the pull-wire wheel anchors. The force measurement(s) can then be conveyed to the user via one or more vibration motors to create haptic feedback (vibration location and magnitude can vary depending on the sensor(s) detecting a force exceeding predefined thresholds and/or the magnitude of the force measurement). The force measurements can also be conveyed to the user via a graphical user interface of an associated processing system, via illumination of one or more of the indicator lights, and/or an audible warning/alarm. Pull-wire tension measurements can also be used to identify if a particular steering device 110 needs to be calibrated/refurbished by identifying significant drop offs in the maximum actuation force at the maximum motor range when compared to the values from original calibration/use.

In cases when steering into tight and complex anatomies are involved, there is a potential need to separate the intravascular device 102 from the steering device 110 (e.g., where the steering device is stuck actuated in a specific direction and angle that prevents safe withdrawal of the intravascular device). Accordingly, the steering device 110 can include features to facilitate the disengagement of the intravascular device 102 from the steering device 110 for safe removal of the intravascular device 102 from the patient. For example, the steering device can include electrical, software, and/or mechanical failsafe components. An electrical failsafe can include an on/off switch or a physical reset button to reset the software logic/electrical hardware should the software/hardware hang while the device is being used. A mechanical failsafe can include a built-in blade within the housing 112 that when actuated/pressed through a shallow cavity from an outside surface of the housing 112 will cut the pull-wires 123 and 125 prior to the wheels, releasing all tension acting on the intravascular device 102 and allowing the intravascular device 102 to return to a relaxed neutral position for removal. Similarly, the attachable modular shaft adapter described above (i.e., where the adaptor 138 is part of a separate component that can be coupled to the housing 112) can simultaneously function as a mechanical failsafe. In this regard, should the intravascular device 102 need to be relaxed and the pull-wire tension released, the user can simply disconnect the modular shaft adaptor and the pull-wire mating interfaces along with it to release the tension.

Figure 8:
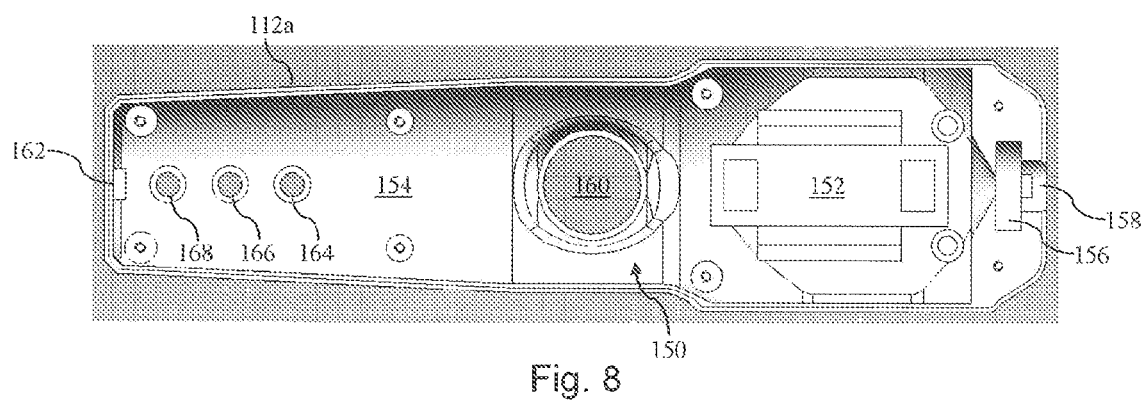
FIG. 8 is a bottom view of a top portion of a housing of the handheld steering device.
Figure 9:
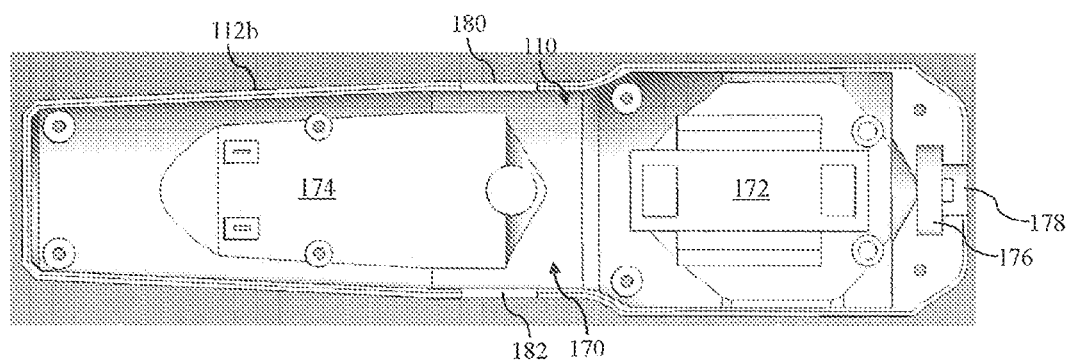
FIG. 9 is a top view of a bottom portion of a housing of the handheld steering device.

FIGS. 8 and 9 illustrate additional features of the housing 112. The housing 112 includes a top portion 112a and a bottom portion 112b. The top and bottom portions 112a and 112b are configured to couple to one another to define housing 112. In this regard, any suitable means of coupling may be utilized, including interlock, snap-fit, mechanical fasteners, adhesives, and/or combinations thereof. Each of the top and bottom portions 112a and 112b includes features sized and shaped to interface with the other components of the steering device.

For example, the top portion 112a includes a cavity 150 having a portion 152 to receive pull-wire wheels 122 and 124, pull-wires 123 and 125, motors 126 and 128, mounting structures 130 and 132, and guide pins 134 and 136. The cavity 150 of the top portion 112a also includes a portion 154 sized and shaped to receive the microcontroller 140 and the mounting structure 142. The distal section of the top portion 112a includes an opening 158 and a recess 156. The top portion 112a includes an opening 160 sized to allow the steering controller 118 to pass through, as well as openings 164, 166, and 168 for indicator lights 144, 146, and 148.

The bottom portion 112b includes a cavity 170 having a portion 172 to receive pull-wire wheels 122 and 124, pull-wires 123 and 125, motors 126 and 128, mounting structures 130 and 132, and guide pins 134 and 136. The cavity 170 of the bottom portion 112b also includes a portion 154 sized and shaped to receive the microcontroller 140 and the mounting structure 142. The distal section of the bottom portion 112b includes an opening 178 and a recess 176. Together, the recesses 156 and 176 define a cavity in which the adaptor 138 is received. Similarly, the openings 158 and 178 define an opening through which the intravascular device 102 can be inserted into the steering device 110 and, more specifically, through which the proximal portion of the intravascular device 102 can extend through the bore in the adaptor 138. Likewise, the cavities 150 and 170 define the spaces for receiving and mounting the other components of the steering device 110. As noted above, the housing 112 is sized and shaped for grasping by a single hand of a user and may have many different geometries suitable for handheld use other than those shown in the present disclosure.

The steering device 110 can be configured to communicate with one or more external devices and/or processing systems. In this regard, the communications with the external devices and/or processing systems can be utilized to control operation of the steering device 110, provide feedback on the steering/actuations imparted by the steering device, and/or receive data from sensing elements associated with the intravascular device 102 and/or steering device 110. It is understood that any communication pathway between the steering device 110 and the external devices and/or processing systems may be utilized, including physical connections (including electrical, optical, and/or fluid connections), wireless connections, and/or combinations thereof. In that regard, it is understood that the connection is wireless in some instances. As such, the microcontroller 140 can include or be in communication with a wireless transceiver positioned within the housing 112. In some instances, the connection includes a communication link over a network (e.g., intranet, internet, telecommunications network, and/or other network). In that regard, it is understood that the external devices and/or processing systems can be positioned remote from a procedure room where the steering device 110 is being used in some instances. Having the connection include a connection over a network can facilitate communication between the steering device 110 and the external devices and/or processing systems regardless of whether the external devices and/or processing systems are in an adjacent room, an adjacent building, or in a different state/country. Further, it is understood that the communication pathway between the steering device 110 and the external devices and/or processing systems is a secure connection in some instances. Further still, it is understood that, in some instances, the data communicated over one or more portions of the communication pathway between the steering device 110 and the external devices and/or processing systems is encrypted.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular steering device, comprising:
  a housing sized and shape for grasping by a hand of a user, the housing including a proximal portion and a distal portion, wherein the distal portion includes an opening sized and shaped to receive an intravascular device;
  a steering controller coupled to the housing to receive inputs from the user and to provide electrical signals in response thereto; and
  an actuator positioned within the housing and in communication with the steering controller, the actuator interfacing with the proximal end of the intravascular device based on inputs to the steering controller to steer a distal end of the intravascular device, the actuator comprising:
- a first pull-wire wheel coupled to the housing;
- a second pull-wire wheel coupled to the housing;
- a first pull-wire anchored to the first pull-wire wheel such that rotation of the first pull-wire wheel adjusts tension on the first pull-wire to manipulate the proximal end of the intravascular device in a first direction;
- a second pull-wire anchored to the second pull-wire wheel such that the rotation of the second pull-wire wheel adjusts tension on the second pull-wire to manipulate the proximal end of the intravascular device in a second direction that is different from the first direction; and
- a motor configured to rotate the first and second pull-wire wheels in response to the electrical signals received from the steering controller and thereby move the distal end of the intravascular device in the first and second directions in response to the inputs from the user.

2. The intravascular steering device of claim 1, wherein the steering controller includes a joystick.

3. The intravascular steering device of claim 1, wherein the actuator further includes:
- a mechanism for controlling movement in a third direction in response to the electrical signals received from the steering controller, the third dimension being perpendicular to the first and second directions.

4. The intravascular steering device of claim 1, wherein the actuator further includes:
- a mechanism for controlling rotation of the intravascular device about a longitudinal axis of the intravascular device in response to the electrical signals received from the steering controller.

5. The intravascular steering device of claim 1, wherein the first and second pull-wire wheels are parallel to each other, and wherein the intravascular steering device further comprises at least one steering pin configured to guide and redirect at least one of the first pull-wire and the second pull-wire.

6. The intravascular steering device of claim 1, wherein the steering controller further comprises:
- a microcontroller positioned within the housing and in communication with the actuator, wherein the microcontroller translates the inputs from the user into the into electrical signals.

7. The intravascular steering device of claim 1, further comprising:
- a haptic feedback device positioned within the housing, the haptic feedback device configured to provide a haptic alert to a user when a force on the intravascular device exceeds a threshold.

8. The intravascular steering device of claim 7, wherein the force on the intravascular device is measured by at least one of:
- a sensor within the housing; or
- a sensor within the intravascular device.

9. The intravascular steering device of claim 1, further comprising:
- a rechargeable power supply positioned within the housing;
- and a wireless transceiver positioned within the housing.

10. The intravascular steering device of claim 1, further comprising an adaptor positioned within the opening of the housing, the adaptor including a bore that is sized and shaped to allow a proximal end of the intravascular device to pass therethrough.

11. The intravascular steering device of claim 10 wherein the adaptor is removable and replaceable with other adaptors having differently sized bores to accommodate different intravascular devices.

12. An intravascular steering device, comprising:
- a housing sized and shaped for grasping by a hand of a user, the housing including a proximal portion and a distal portion, wherein the distal portion includes an opening sized and shaped to receive an intravascular device;
- a steering controller coupled to the housing to receive mechanical inputs from a user of the intravascular steering device and to provide electrical signals in response thereto; and
- an actuator positioned within the housing and in communication with the steering controller, the actuator interfacing with the proximal end of the intravascular device based on inputs to the steering controller to steer a distal end of the intravascular device, the actuator comprising:
- a first pull-wire wheel coupled to the housing;
- a second pull-wire wheel coupled to the housing;
- a first pull-wire anchored to the first pull-wire wheel such that rotation of the first pull-wire wheel adjusts tension on the first pull-wire to manipulate the proximal end of the intravascular device in a first dimension;
- a second pull-wire anchored to the second pull-wire wheel such that rotation of the second pull-wire wheel adjusts tension on the second pull-wire to manipulate the proximal end of the intravascular device in a second dimension that is substantially perpendicular to the first dimension; and
- a motor configured to rotate the first and second pull-wire wheels in response to the electrical signals received from the steering controller and thereby move the distal end of the intravascular device in the first dimension in the second dimension.

13. The intravascular steering device of claim 12, wherein the first and second pull-wire wheels are parallel to each other, and wherein the intravascular steering device further comprises at least one steering pin configured to guide and redirect at least one of the first pull-wire and the second pull-wire.

14. The intravascular steering device of claim 12, further comprising an adaptor positioned within the opening of the housing, the adaptor including a bore that is sized and shaped to allow a proximal end of the intravascular device to pass therethrough.

15. The intravascular steering device of claim 12 wherein the adaptor is removable and replaceable with other adaptors having differently sized bores to accommodate different intravascular devices.

16. The intravascular steering device of claim 12 wherein the first and second pull-wire wheels are rigidly coupled to the housing to permit rotation but not translation of the wheel.

* * * * *